United States Patent [19]

Reber

[11] Patent Number: 4,944,861

[45] Date of Patent: Jul. 31, 1990

[54] OXYGEN SENSING PROBE HAVING IMPROVED SENSOR TIP AND TIP-SUPPORTING TUBE

[75] Inventor: Eric J. Reber, Rockford, Ill.

[73] Assignee: Barber-Colman Company, Rockford, Ill.

[21] Appl. No.: 332,052

[22] Filed: Apr. 3, 1989

[51] Int. Cl.⁵ ............................................. G01N 27/417
[52] U.S. Cl. ..................................... 204/428; 204/421; 204/427
[58] Field of Search ........................... 204/15, 421–429

[56] References Cited

U.S. PATENT DOCUMENTS

| | | |
|---|---|---|
| 3,616,407 | 10/1971 | Ergell . |
| 3,619,381 | 11/1971 | Fitterer . |
| 3,723,279 | 3/1973 | Fruehan et al. . |
| 4,019,974 | 4/1977 | Weyl et al. ............................ 204/15 |
| 4,046,661 | 9/1977 | Stringer et al. ...................... 204/426 |
| 4,193,857 | 3/1980 | Bannister et al. . |
| 4,240,891 | 12/1980 | Bannister ............................. 204/426 |
| 4,559,126 | 12/1985 | Mase et al. ........................... 204/426 |
| 4,560,463 | 12/1985 | Frey et al. ............................ 204/427 |
| 4,588,493 | 5/1986 | Blumenthal et al. . |

Primary Examiner—T. Tung
Attorney, Agent, or Firm—Leydig, Voit & Mayer

[57] ABSTRACT

An oxygen sensing probe of the type in which a sensor tip made of a solid electrolyte is secured within a supporting tube by an hermetic seal. The tip is made of yttria-stabilized zirconia; the tube is made of magnesium-aluminate spinel, calcia and zirconia; and the tip and the tube are bonded together by a fusion weld consisting of a eutectic mixture of the tip material and the tube material. The coefficient of thermal expansion of the tube material very closely matches that of the tip material so as to prevent the seal from cracking when the probe is cycled rapidly and repeatedly through a wide temperature range. A frustoconical shoulder on the sensor tip engages a slotted frustoconical seat within a tubular outer conductor to establish good electrical contact between the tip and the electrode while allowing gas to circulate freely past the tip.

12 Claims, 2 Drawing Sheets

OXYGEN SENSING PROBE HAVING IMPROVED SENSOR TIP AND TIP-SUPPORTING TUBE

BACKGROUND OF THE INVENTION

This invention relates generally to a probe for measuring the concentration of oxygen in fluids. More particularly, the invention relates to a probe having a sensor tip defining a solid electrolyte which is in contact on one side with a known reference fluid and on the opposite side with the fluid whose oxygen content is to be measured. In such a probe, a voltage is generated across conductors on the two sides of the electrolyte as oxygen ions conduct through the electrolyte. The magnitude of the voltage is a function of the temperature of the electrolyte and of the log of the ratio of the oxygen partial pressures on the two sides of the electrolyte.

An oxygen-measuring probe of this general type is disclosed in Bannister et al U.S. Pat. No. 4,193,857. In that probe, a sensor tip formed of a solid electrolyte material is concentric with one end portion of an elongated tube and is secured to the tube by an hermetic seal which isolates the reference fluid from the fluid being measured.

Difficulty is encountered in producing an hermetic seal which can withstand rapid and repeated cycling through a wide range of temperatures. In an effort to produce a reliable seal, Bannister et al modify a conventional solid electrolyte material with another material to form a composite sensor tip which purportedly lends itself to being sealed in an alumina tube. This construction, however, results in an adulterated sensor tip which can lead to imprecise sensing and particularly at lower temperatures where the resistance to ion flow through the sensor tip is relatively high. In spite of the adulterated composition of the sensor tip, cracking still can occur at the seal between the sensor tip and the alumina tube. Moreover, the sensor tip is relatively expensive because of the need to modify the composition of a conventional sensing tip which can be purchased on the open market.

SUMMARY OF THE INVENTION

The general aim of the present invention is to provide a new and improved oxygen measuring probe which, when compared with prior probes of the same general type, is comparatively inexpensive, is capable of experiencing a longer service life without need of repair, and is capable of producing a precise output signal even when the temperature of the fluid being sensed is relatively low.

A more detailed object of the invention is to achieve the foregoing by providing a probe which utilizes a commercially available sensor tip of conventional material in conjunction with a supporting tube made of a material which is specially formulated to enable an hermetic seal of high integrity and reliability to be established between the sensor tip and the tube.

Still another object is to construct the sensor tip and the outer conductor in such a way as to establish good electrical contact between the two while allowing fluid to circulate freely past the tip and between the outer conductor and the inner tube.

These and other objects and advantages of the invention will become more apparent from the following detailed description when taken in conjunction with the accompanying drawings.

DETAILED DESCRIPTION OF THE PREFERRED EMBODIMENT

Figure 1:
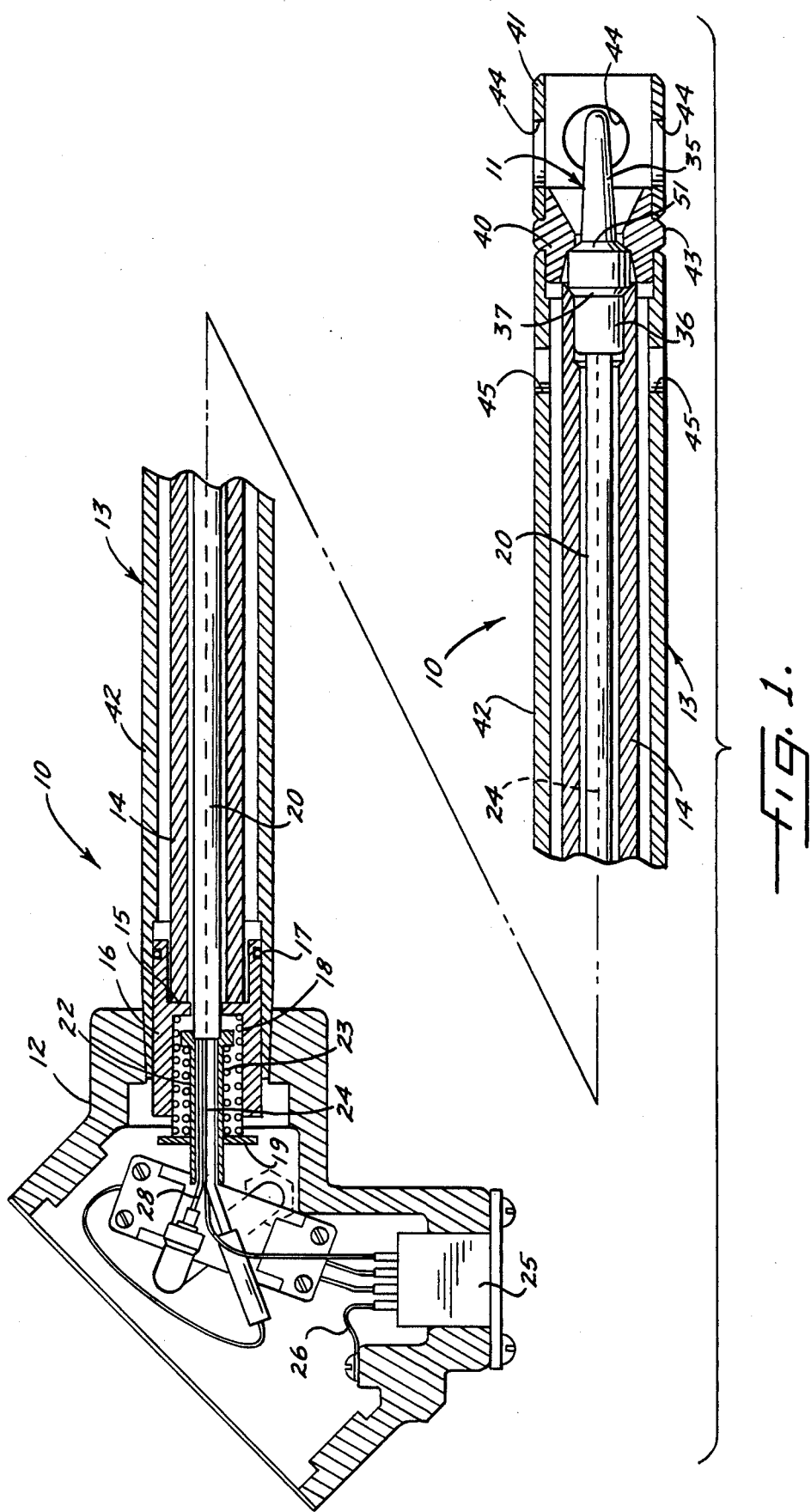
FIG. 1 is a sectional view taken axially through a new and improved oxygen measuring probe incorporating the unique features of the presesnt invention.

For purposes of illustration, the invention has been shown in the drawings as being incorporated in a probe 10 for measuring the oxygen content of a fluid. The probe may, for example, be used in connection with a heat treating furnace to measure the concentration of oxygen in the gaseous treatment atmosphere in the furnace. The probe also may be used to measure the oxygen content of a liquid such as molten copper.

The probe 10 operates on a well known principle involving the use of a sensor tip 11 made of a solid electrolyte material. One side of the sensor tip is exposed to the gas whose oxygen content is to be measured while the other side of the tip is exposed to a known reference gas. Conductors are connected to the two sides of the sensor tip. At elevated temperatures, oxygen in the gas to be measured ionizes and conducts through the sensor tip to produce a voltage across the conductors. Such voltage changes as a function of the temperature of the sensor tip and of the log of the ratio of the partial pressures of the reference gas and the gas being measured. By detecting the temperature of the sensor tip and the voltage across the tip, the oxygen content of the gas can be determined in a well known manner through the use of conventional instrumentation.

As shown in FIG. 1, the probe 10 includes an electrically conductive housing 12 which supports an elongated tubular member 13 made of stainless steel, nickel alloy or the like. The tube 13 projects forwardly from the housing and serves as one of the aforementioned conductors for the probe 10. In addition, the forward end portion of the tube serves as a protective sheath for the sensor tip 11 and prevents the tip from being damaged by objects in the vicinity of the free end of the tube.

Located within the outer tube 13 is an electrically non-conductive tube 14 whose forward free end portion supports the sensor tip 11. The rear end portion of the inner tube 14 butts against an annular shoulder 15 formed within a sleeve 16 which is telescoped slidably into the rear end portion of the outer tube 13. An 0-ring 17 establishes a gas-tight seal between the sleeve and the outer tube. The shoulder 15 of the sleeve 16 is urged forwardly into engagement with the tube 14 by a coil spring 18 which is compressed between the rear side of the shoulder and a fixed plate 19 secured within the housing 12.

Figure 2:
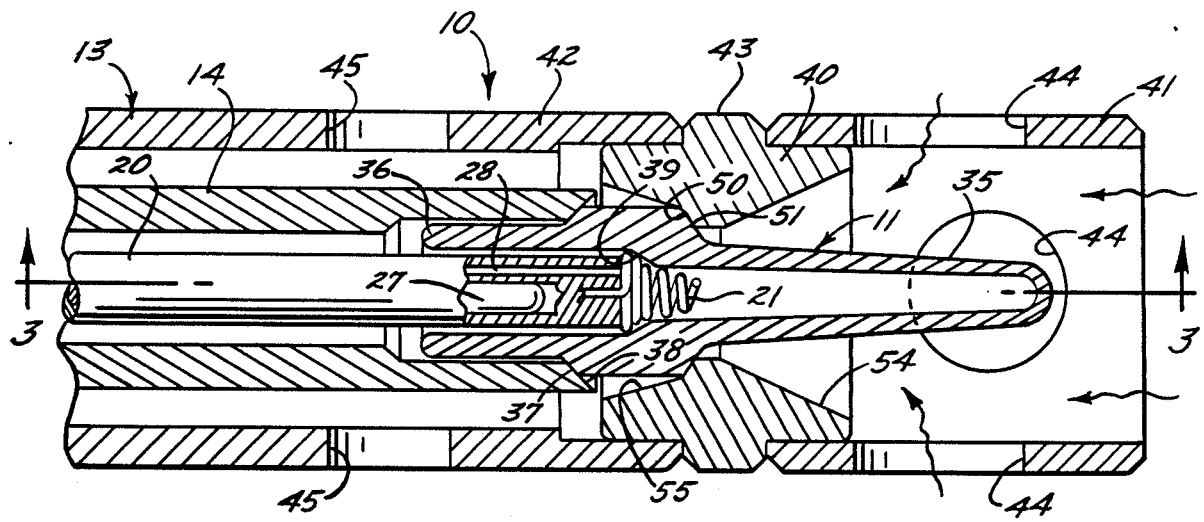
FIG. 2 is an enlarged sectional view of the sensing portion of the probe shown in FIG. 1.

A central insulating tube 20 extends through the tube 14 and its forward end supports a conductor 21 (FIG. 2) in the form of a conically coiled wire. The rear end of the insulating tube is secured within a flanged bushing 22 (FIG. 1) which extends slidably through the plate 19 and which is urged forwardly by a coil spring 23. The tube 20 and the bushing 22 serve as a protective sheath for a wire 24 which extends from the conical conductor 21 and out of the inner end of the bushing to a quickconnect electrical jack 25 located in one wall of the housing 12. The outer tubular conductor 13 is conductively coupled with the housing 12 which, in turn, is connected electrically to the jack 25 by a wire 26.

A thermocouple 27 (FIG. 2) extends through the bushing 22 and into the insulating tube 20 and is located in proximity to the sensor tip 11 so as to measure the temperature at the tip. In addition, a tube 28 which communicates with a supply of air or other reference gas extends into the insulating tube 20 and delivers a flow of reference gas to the sensor tip.

In order for the probe 10 to function properly, it is necessary to isolate the reference gas from the gas whose oxygen content is to be measured. This is achieved by establishing an hermetic seal between the sensor tip 11 and its supporting tube 14. As a result of the seal, all of the reference gas is confined within the tube 14 and within the inside of the sensor tip while the gas being measured is confined to the outside of the tube 14 and the sensor tip.

In accordance with the primary aspect of the present invention, the tube 14 is specially formulated to enable an extremely reliable and temperature-resistant hermetic seal to be established between the tube and a commercially available and unadulterated sensor tip 11 which is conventionally used as a sensor in automobiles. As will become more apparent subsequently, the seal can withstand very high temperatures and, because the sensor tip is sealed to the tube without modifying the material of the tip, the sensor is effective to precisely signal the oxygen content of gases of widely varying temperatures.

The sensor tip 11 which is preferred for use herein is a tip sold by Autolite Division of Allied Automotive. Such a tip is formed of a ceramic material consisting of 92% by weight zirconia ($ZRO_2$) and 8% by weight yttria ($Y_2O_3$) A tip of this type is preferred since it is commercially available and thus relieves the manufacturer of the probe 10 from making a specially formulated component. It will be appreciated, however, that the tip could be made of other metal oxides such as hafnia ($HfO_2$), thoria ($ThO_2$) or scandia ($Sc_2O_3$) Such metal oxides may be stabilized by calcia (CaO), magnesia (MgO) or yttria ($Y_2O_3$) ranging from 2.5% to 22% by weight of the total weight of the sensor. The sensor tip is hollow and the major portions of its inner and outer surfaces are coated with a high temperature and electrically conductive noble metal. Platinum is the preferred coating although, for certain tips, nickel or palladium could be used in place of platinum. The coating is electrically conductive and is capable of serving as an electrode as well as a catalyst promoting the ionization of oxygen.

In carrying out the invention, the inner tube 14 is made of a ceramic material consisting of at least 40% by weight of magnesium-aluminate spinel ($MgAl_2O_4$) and preferably having less than 4 by weight of free alumina ($Al_2O_3$) The constituents of the preferred tube are, by weight, about 48% alumina bound together with about 21% magnesia to form a magnesium-aluminate spinel, about 18% zirconia and about 12% calcia. The preferred tube contains less than 1% free alumina. A base material consisting of about 85% by weight $MgAl_2O_4$ and 15% by weight of 3% magnesium-stabilized zirconia is available commercially. To this base material is added calcia and additional magnesium-stabilized zirconia to increase the coefficient of thermal expansion of the base material to a value near that of the sensor tip 11 and to arrive at the preferred tube material described above.

An hermetic seal is established between the sensor tip 11 and the tube 14 by telescoping the tip into the tube and by heating the assembly with propylene and acetylene torches while the assembly is being rotated about its own axis at a speed of about 180 RPM. When the temperature of the joint reaches about 3150 degrees F., a liquid phase forms at the interface of the tip and the tube and, upon cooling, bonds the two together with a gas-tight seal. The seal is an eutectic mixture in that its melting point of 3150 degrees F. is lower than the melting point (4710 degrees F.) of the tip 11 and the melting point (approximately 3350 degrees F.) of the tube 14.

The preferred tube 14 is thermally and chemically compatible with the preferred sensor tip 11. The coefficient of thermal expansion of the tube is within 2% of that of the sensor tip throughout the operating temperature range of 70°–3,000 degrees F. of the probe 10. As a result, the seal at the interface of the tube and the tip is reliable and does not crack as the probe 10 is cycled repeatedly and rapidly through the operating temperature range. The seal is sufficiently tight that, when the tube is pressurized to 30 p.s.i. at room temperature, the maximum rate of leakage at the tube/tip interface is 2 ml./min. Moreover, since the seal is an eutectic and may be formed at about 3150 degrees F., the tip may be coated with platinum (melting point of about 3200 degrees F.) before the tip is assembled with and sealed to the tube. As a result, the platinum coating is of greater integrity and thus the platinum is less likely to dislodge during service use.

By virtue of the material used for the tube 14, there is no need to modify the solid electrolyte material of the purchased sensor tip 11 in order to obtain a tight and reliable seal between the tube and the tip. Because the tip is unadulterated, there is consistency of sensing over a wide temperature range and also between the tips of different probes. The ionic conductivity of the tip is not adversely affected by materials added to the optimum tip material used by the tip manufacturer. Moreover, the expense of adding materials to the tip is eliminated.

From a mechanical standpoint, the tip 11 includes a sensing portion 35 (FIG. 2) in the form of a hollow frustoconical body having a wall thickness of about 0.060" and no greater than 0.100" in order that the sensing portion will be of low electrical resistance. An unadulterated sensing tip 11 having a sensing portion 35 with a wall thickness of about 0.060" is capable of reliably signaling the oxygen content of a gas at a temperature as low as 800 degrees F.

The end portion of the sensor tip 11 opposite the sensing portion 35 is defined by a cylindrical shank portion 36 (FIG. 2) which is telescoped into the end portion of the tube 14 with a tight fit. Between the portions 35 and 36, the sensor tip is formed with a frustoconical shoulder 37 which engages an annular frustoconical seat 38 formed at the end of the tube 14. The hermetic seal is established between the shoulder 37 and the seat 38. The shoulder 37 and the outside surface of the shank 36 are not coated with platinum nor is there a coating on the inside surface of that portion of the shank which is located within the tube 14.

The conical inner conductor 21 (FIG. 2) engages an annular frustoconical seat 39 (FIG. 2) which is formed on the inside of the sensor tip 11 between the sensing portion 35 and the shank 36. Good electrical contact between the conductor 21 and the seat 39 is established by virtue of the spring 23 urging the inside tube 20 forwardly and biasing the conductor against the seat.

In accordance with another aspect of the invention, means are provided for establishing good electrical contact between the sensor tip 11 and the outer tubular conductor 13 while permitting gas to circulate freely past the tip. Herein, these means comprise a sleeve 40 made of stainless steel or nickel alloy and forming part of the outer tubular conductor 13, the latter also including two axially spaced tubes 41 and 42 located on opposite sides of the sleeve. The sleeve is telescoped into the tubes, is formed with a flange 43 located between the ends of the tubes, and is welded rigidly to the tubes at the junctions of the flange with the tubes. The tube 41 is formed with a series of angularly spaced air passages 44 adjacent one end of the sleeve 40 while the tube 42 is formed with similar passages 45 adjacent the other end of the sleeve.

Figure 3:
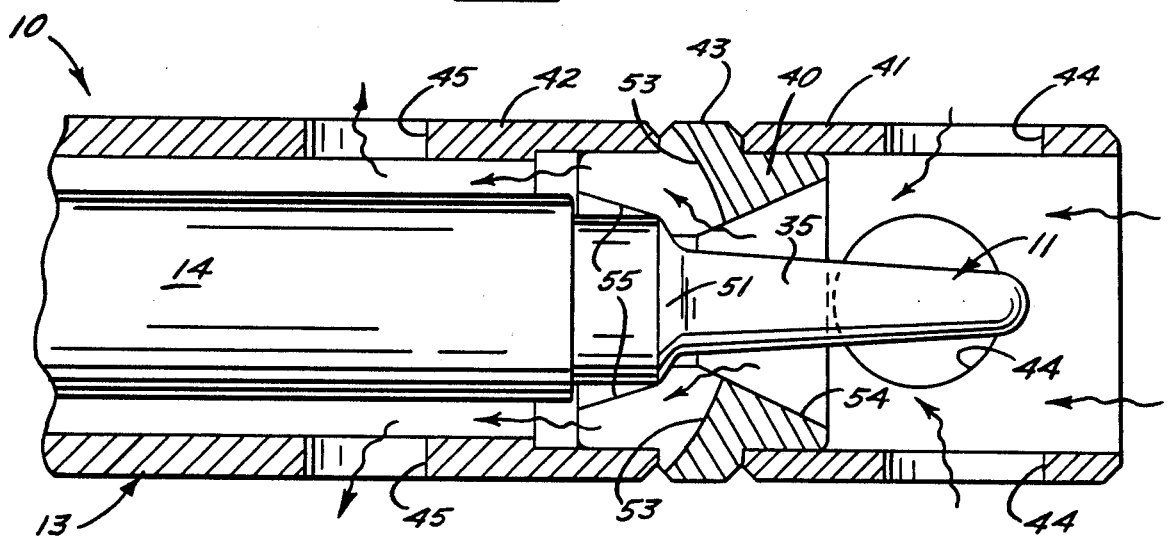
FIG. 3 is a fragmentary cross-section taken substantially along the line 3—3 of FIG. 2.

Pursuant to the invention, the sleeve 40 is formed with an annular frustoconical seat 50 (FIG. 2) which engages a frustoconical shoulder 51 on the sensor tip 11 adjacent the rear end of the sensing portion 35. The seat is segmented in that it is formed with a series of angularly spaced slots or passages 53 (FIG. 3). Such passages communicate with a rearwardly tapering throat 54 formed in the forward end portion of the sleeve 40 and with a rearwardly flaring throat 55 formed in the rear end portion of the sleeve.

With the foregoing arrangement, the spring 18 pushes the tube 14 and the sensor tip 11 forwardly to press the shoulder 51 of the sensor tip into good electrical contact with the seat 50 of the sleeve 40 and thereby establish a conductive path between the inner and outer conductors 21 and 13 by way of the tip. Gas flowing into the end of the tube 41 and the passages 44 therein circulates freely past the sensor tip by flowing through the slots 53 in the seat 50 of the sleeve 40, by flowing within the annular space between the tubes 14 and 42 and then by flowing out of the passages 45 in the latter tube. Such circulation prevents the gas in the immediate vicinity of the sensor tip from becoming stagnant and enables the tip to measure the oxygen content of transient samples of the overall volume of gas.

What is claimed:

1. A probe for measuring the concentration of oxygen in fluids, said probe comprising an outer tube defining an outer conductor, an inner tube coaxial with and spaced inwardly from said outer tube, a sensor tip secured to said inner tube and composed of solid electrolyte material, two electrodes disposed on opposite sides of said sensor tip, and an inner conductor in electrical contact with one of said electrodes, said probe being characterized in that an electrically conductive sleeve is telescoped tightly into one end portion of said outer tube in electrical contact therewith and is telescoped over said sensor tip in electrical contact with the other of said electrodes, one end portion of said sleeve being formed with an annular frustoconical seat, said tip being formed with a frustoconical shoulder located in facetoface mating engagement with the seat of said sleeve, the seat of said sleeve being defined by a series of angularly spaced segments having passages therebetween to permit fluid to flow out of the inside of said sleeve and along the outside of said inner tube.

2. A probe as claimed in claim 1 in which said sensor tip is hollow and tapers toward a free end portion, the wall thickness of said free end portion being no greater than 0.060 inches.

3. A probe as defined in claim 2 in which said one end of said inner tube is defined by an annular and substantially frustoconical seat, a substantially frustoconical shoulder on said sensor tip and mating it face-to-face engagement with the seat of said inner tube, and a bond between the last-mentioned shoulder of said sensor tip and the seat of said inner tube and establishing an hermetic seal between said sensor tip and said inner tube.

4. A probe as defined in claim 3 in which said seal comprises an eutectic mixture of the material of said inner tube and the material of said tip.

5. A probe as defined in claim 11 in which said tip and said inner tube are made of ceramic material and are joined by an hermetic seal, the ceramic material of said tip being 100% by weight of an oxygen ion conductor consisting essentially of a metal oxide and a stabilizing material, said metal oxide consisting of between 78% and 97.5% by weight of the ceramic material of said tip and being selected from the group consisting of hafnia, scandia, thoria and zirconia, said stabilizing material consisting of between 22% and 2.5% by weight of the ceramic material of the tip and being selected from the group consisting of calcia, magnesia and yttria, the ceramic material of said inner tube comprising at least 40% by weight of a magnesiumaluminate spinel, said hermetic seal being formed by an eutectic mixture of the ceramic material of said tip with the ceramic material of said inner tube.

6. A probe as defined in claim 5 in which said metal oxide is zirconia and in which said stabilizing material is yttria.

7. A probe as defined in claim 6 in which the ceramic material of said tip has portions coated with a metal selected from the group consisting of palladium and platinum to define said electrodes, the melting point of said eutectic mixture being less than the melting point of said metal.

8. A probe as defined in claim 7 in which said inner tube comprises about 70% by weight magnesium-aluminate spinel, about 12% by weight calcia and about 18% by weight magnesium-stabilized zirconia.

9. A probe as defined in claim 5 in which the ceramic material of said tip consists essentially of about 92% by weight zirconia and about 8% by weight yttria.

10. A probe as defined in claim 5 in which said inner tube also comprises calcia and magnesiumstabilized zirconia and comprises less than 4% by weight free alumina.

11. A probe as defined in claim 10 in which said inner tube comprises about 70% by weight magnesium-aluminate spinel, about 12% by weight calcia and about 18% by weight magnesium-stabilized zirconia.

12. A probe as defined in claim 11 in which said tip and said inner tube are made of ceramic material and are joined by an hermetic seal, said tip having portions coated with platinum and defining said electrodes, the ceramic material of said tip consisting of 100% by weight yttria-stabilized zirconia having approximately 92% by weight zirconia and having approximately 8% by weight yttria; the ceramic material of said inner tube consisting essentially of about 70% by weight $MgAl_2O_4$, about 18% by weight $ZrO_2$, and about 12% by weight $CaO$, said hermetic seal being formed by an eutectic mixture of the ceramic material of said tip and the ceramic material of said inner tube and produced by heating said tip and said inner tube to a temperature below the melting point of said platinum while the ceramic material of the tip and the ceramic material of the inner tube are in contact with one another.

* * * * *